United States Patent [19]

Baker et al.

[11] Patent Number: 4,797,407
[45] Date of Patent: Jan. 10, 1989

[54] FUNGICIDAL PYRIDYL CARBAMATES

[75] Inventors: Don R. Baker, Orinda; Keith H. Brownell, San Jose, both of Calif.

[73] Assignee: ICI Americas Inc., Wilmington, Del.

[21] Appl. No.: 114,810

[22] Filed: Oct. 29, 1987

[51] Int. Cl.⁴ .................... C07D 213/75; A01N 43/40
[52] U.S. Cl. ...................................... 514/346; 514/336; 514/352; 546/268; 546/283; 546/292; 546/305; 546/309
[58] Field of Search ............... 546/292, 268, 283, 305, 546/309, ; 514/346, 352, 336

[56] References Cited

U.S. PATENT DOCUMENTS 4,375,546  3/1983  Pawloski ........................ 546/292
4,672,070  6/1987  Takahashi et al. ................ 514/346

*Primary Examiner*—Alan L. Rotman
*Attorney, Agent, or Firm*—Michael J. Bradley

[57] ABSTRACT

Novel fungicidal pyridyl carbamates having the formula

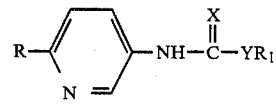

wherein
R is selected from the group consisting of halogen such as chlorine, fluorine and bromine, $C_1$–$C_3$ alkoxy such as propoxy, ethoxy and methoxy, preferably methoxy, —$CF_3$, $C_3$–$C_4$ alkenyloxy and $C_1$–$C_3$ haloalkoxy;
$R_1$ is selected from the group consisting of $C_1$–$C_6$ alkyl, preferably methyl; $C_3$–$C_6$ cycloalkyl, benzyl, $C_1$–$C_3$ haloalkyl and $C_3$–$C_8$ cyclic, straight or branched alkoxyalkyl;
X is either oxygen or sulfur; Y is either oxygen or sulfur; and fungicidally acceptable organic and inorganic salts thereof. These compounds provide excellent control of fungal growth.

9 Claims, No Drawings

FUNGICIDAL PYRIDYL CARBAMATES

BACKGROUND OF THE INVENTION

Fungal infection of crops such as barley, rice, tomatoes, wheat, beans, roses, grapes and other agriculturally important crops can cause heavy losses in both quantity and quality of agricultural products. It is therefore extremely desirable to have means of preventing, controlling or eliminating fungal growth. Much preventive spraying with commercial fungicides is conducted to attempt to prevent the establishment and growth of fungi on agriculturally important crops. It would also be desirable to have a curative fungicide which, on detection of fungal infection, could control the fungi and eliminate the deleterious effects by use of a post-infection curative spray.

SUMMARY OF THE INVENTION

Novel fungicidal pyridyl carbamates having the formula

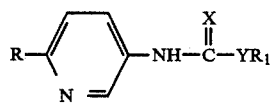

wherein

R is selected from the group consisting of halogen such as chlorine, fluorine and bromine, $C_1$–$C_3$ alkoxy such as propoxy, ethoxy and methoxy, preferably methoxy, —$CF_3$, $C_3$–$C_4$ alkenyloxy and $C_1$–$C_3$ haloalkoxy;

$R_1$ is selected from the group consisting of $C_1$–$C_6$ alkyl, preferably methyl; $C_3$–$C_6$ cycloalkyl, benzyl, $C_1$–$C_3$ haloalkyl and $C_3$–$C_8$ cyclic, straight or branched alkoxyalkyl;

X is either oxygen or sulfur; Y is either oxygen or sulfur; and fungicidally acceptable organic and inorganic salts thereof which are highly effective fungicides for use both as preventive and curative fungicides are disclosed herein.

The term "fungicide" is used to mean a compound which controls fungal growth. "Controls" includes prevention, destruction and inhibition of fungal growth. The term "curative" is meant to refer to a post-infection application of a fungicide which establishes control of fungal infection and prevents development of deleterious effects of the fungi on the host crop.

DETAILED DESCRIPTION

The novel fungicidal compounds of this invention are pyridyl carbamates having the general formula

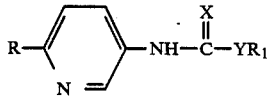

wherein

R is selected from the group consisting of halogen such as chlorine, fluorine and bromine, $C_1$–$C_3$ alkoxy such as propoxy, ethoxy and methoxy, preferably methoxy, —$CF_3$, $C_3$–$C_4$ alkenyloxy and $C_1$–$C_3$ haloalkoxy;

$R_1$ is selected from the group consisting of $C_1$–$C_6$ alkyl, preferably methyl; $C_3$–$C_6$ cycloalkyl, benzyl, $C_1$–$C_3$ haloalkyl and $C_3$–$C_8$ cyclic, straight or branched alkoxyalkyl;

X is either oxygen or sulfur; Y is either oxygen or sulfur; and fungicidally acceptable organic and inorganic salts thereof which are highly effective fungicides for use both as preventive and curative fungicides are disclosed herein.

By the term "halogen" is meant bromine, fluorine and chloride.

By the term "$C_1$–$C_3$ alkoxy" is meant methoxy, ethoxy, propoxy and isopropoxy.

By the term "$C_1$–$C_3$ haloalkoxy" is meant halogen substituted methoxy, ethoxy, propoxy and isopropoxy.

By the term "$C_3$–$C_4$ alkenyloxy is meant such types as allyloxy, crotyloxy and methallyloxy.

The compounds of this invention can be generally prepared by reacting a properly substituted aminopyridine with a properly substituted chloroformate in an inert solvent such as dichloromethane in a suitable reactor. It is desirable to maintain an acid scavenger such as pyridine in the reaction vessel. The reaction generally will proceed at room temperature but will operate at a temperature range from $-30°$ to $60°$ C., depending on the substitutions on the amino pyridine and the chloroformate. The reaction should go to completion within 1 to 3 hours. The resulting product is recovered in a conventional manner by washing with an alkali solution such as sodium hydroxide and water, drying over conventional drying agents such as magnesium sulfate, and crystallizing from hexane. Salts of the pyridyl carbamates can be conventionally prepared by reacting at least a molar amount of a Lewis acid with the carbamate. Preferably the reaction is run in a solvent for the carbamate with heating if necessary. The prepared salt is recovered from the reaction mixture by conventional techniques.

Pyridyl carbamates of the invention are basic. The unprotonated nitrogen atom of the pyridyl ring can be protonated by an acid, either organic or inorganic. Representative inorganic acids are hydrochloric, nitric, hydrobromic, sulfuric, sulfamic and phosphoric. Representative organic acids are acetic, trifluoroacetic, benzoic, benzenesulfonic, p-toluenesulfonic, naphthalenesulfonic, phenylphosphonic and organophosphonic. The salts so formed are also fungicidal.

EXAMPLE 1

Preparation of S-Isopropyl-N-(2-methoxy-5-pyridyl)-thiolcarbamate

5-Amino-2-methoxy pyridine (6.5 g, 0.052 mol) was dissolved in methylene chloride (100 ml). To this was added pyridine (4.1 g, 0.052 mol) in one portion followed by the dropwise addition of the isopropyl chlorothiolformate (7.2 g, 0.052 mol) dissolved in methylene chloride (25 ml). The reaction temperature was maintained at 10° C. during the addition by stirring and cooling. The reaction was stirred overnight at room temperature. The reaction mixture was washed with 5% sodium bicarbonate solution, water and then dried over anhydrous magnesium sulfate. The drying agent was filtered off and the filtrate evaporated in vacuo to give a pink solid that was triturated with hexane to give 8.5 g, m.p. 100°–102° C., of the title product as identified by its infra-red (IR), nuclear magnetic resonance spectra (NMR) and mass-spectroscopic (MS) examination.

EXAMPLE 2

Preparation of O-Methyl-N-(2-methoxy-5-pyridyl)-carbamate

5-Amino-2-methoxypyridine (6.0 g, 0.064 mol) was dissolved in methylene chloride (100 ml) followed by addition of pyridine (9.5 g, 0.12 mol). To this solution was added methyl chloroformate (8.3 g, 0.088 mol) dropwise with stirring at approximately 15° C. The addition was exothermic and the reaction was stirring for a further two hours at room temperature. It was then washed with water (2 times), dried over magnesium sulfate, filtered, and evaporated in vacuo to yield an organge solid that was triturated with hexane several times to yield 9.3 g, m.p. 100°–101° C., of the title product as identified by its infra-red and nuclear magnetic resonance spectra and by mass spectroscopic analysis.

EXAMPLE 3

Preparation of O-Methyl-N-(2-methoxy-5-pyridyl)-thionocarbamate

5-Amino-2-methoxypyridine (11 ml, 0.10 mol) was added dropwise to the stirred solution of thiophosgene (8.4 ml, 0.11 mol) and methylene chloride (100 ml) at reflux. Solid immediately formed and the reaction stirred at reflux for one hour and cooled to room temperature. The solid was filtered off, washed with ether to give 9.6 g of the solid, 2-methoxy-5-pyridyl isothiocyanate hydrochloride.

The above 2-methoxy-5-pyridyl isothiocyanate hydrochloride 4.1 g 0.02 mole), methanol (50 ml) and 25% methanolic sodium methoxide (9.1 ml, 0.04 mole) were mixed together. The reaction was exothermic on addition of the sodium methoxide solution to the stirred reaction mixture. The reaction was allowed to stand fir two hours at room temperature and then evaporated in vacuo to a volume of approixmately 100 ml and then diluted with methylene chloride (100 ml), washed with water (100 ml), saturated sodium bicarbonate solution (50 ml), dried over magnesium sulfate, filtered and evaporated in vacuo to yield an oil that crystallized from pentane to give 2.3 g of solid, m.p. 69°–80° C. The structure was confirmed as the title compound by its infrared and nuclear magnetic resonance spectra and by mass spectroscopic analysis.

Representative compounds of this invention and their physical properties are shown in Table I.

TABLE I $$R-\underset{N}{\underset{\parallel}{\bigcirc}}-NH-\overset{X}{\underset{\parallel}{C}}-YR_1$$

| Cmpd. No. | R | $R_1$ | X | Y | Physical Constant $n_D^{30}$ or melting point °C. |
|---|---|---|---|---|---|
| 1 | —OCH$_3$ | —CH(CH$_3$)$_2$ | O | S | 100.0–102.0 |
| 2 | —OCH$_3$ | —CH$_3$ | O | S | 96.0–97.0 |
| 3 | —OCH$_2$CH=CH$_2$ | —C$_2$H$_5$ | O | S | 55.0–58.0 |
| 4 | —OC$_2$H$_5$ | —C$_3$H$_7$ | O | S | 60.0–62.0 |
| 5 | —OC$_4$H$_9$ | —C$_2$H$_5$ | O | S | 55.0–56.0 |
| 6 | —OCH$_3$ | —C$_2$H$_5$ | O | S | 60.0–62.0 |
| 7 | —OCH$_3$ | —CH$_2$—C$_6$H$_5$ | O | S | 92.0–94.0 |
| 8 | —OCH$_3$ | —CH$_3$ | O | O | 100.0–101.0 |
| 9 | —OCH$_3$ | —C$_2$H$_5$ | O | O | 63.0–65.0 |
| 10 | —OCH$_3$ | —CH(CH$_3$)$_2$ | O | O | 64.0–65.0 |
| 11 | —OCH$_3$ | —CH$_2$CH$_2$CH$_2$Cl | O | O | 90.0–92.0 |
| 12 | —OCH$_3$ | —CH$_2$CH(CH$_3$)$_2$ | O | O | 54.0–56.0 |
| 13 | —OCH$_3$ | —C$_6$H$_{11}$ (cyclohexyl) | O | O | 84.0–85.0 |
| 14 | —OCH$_3$ | —C$_5$H$_9$ (cyclopentyl) | O | O | 50.0–55.0 |
| 15 | —OCH$_3$ | —CH(C$_2$H$_5$)$_2$ | O | O | 35.0–36.0 |
| 16 | —OCH$_3$ | —CH(CH$_3$)(C$_2$H$_5$) | O | O | oil |
| 17 | —OCH$_3$ | —CH$_2$—C$_6$H$_5$ | O | O | 54.0–57.0 |
| 18 | —OCH$_3$ | —C$_3$H$_7$ | O | O | 67.0–71.0 |
| 19 | —OCH$_3$ | —CH$_3$ | S | O | 69.0–80.0 |
| 20 | —OCH$_2$CH=CH$_2$ | —CH$_3$ | O | S | 58.0–62.0 |
| 21 | —OCH$_2$CH=CH$_2$ | —CH$_3$ | O | O | 45.0–47.0 |

TABLE I-continued $$R\text{—}\underset{N}{\underset{\parallel}{\diagup\hspace{-0.2em}\diagdown}}\text{—NH—}\overset{X}{\underset{\parallel}{C}}\text{—YR}_1$$

| Cmpd. No. | R | R₁ | X | Y | Physical Constant $n_D^{30}$ or melting point °C. |
|---|---|---|---|---|---|
| 22 | —OCH₃ | —CH₂CH₂OCH₃ | O | O | semi-solid |
| 23 | —OCH₃ | —CH₂—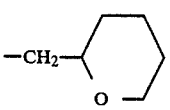 | O | O | 66.0–69.0 |
| 24 | —OCH₃ | —CH₂—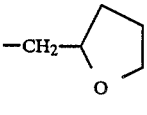 | O | O | brown oil |
| 25 | —OCH₃ | —CH(CH₃)CH(CH₃)₂ | O | O | brown oil |
| 26 | —Cl | —CH₃ | O | O | 115.0–120.0 |
| 27 | —Cl | —CH₃ | O | O | 135.0–137.0 |

EXAMPLE 4

Preventative Spray Evaluation Procedures

Barley Powdery Mildew (PM)

Northern King Sunbar 401 barley seed is planted (12 seeds/2" pot) in a sandy-loam soil seven days prior to testing. The test compound is diluted in a 50/50 acetone/water solution to produce concentrations decreasing from 2250 µg/ml. The test solution is then sprayed onto the barley plants with atomizing sprayers.

Twenty-four hours later, test plants are placed in an inoculation box equipped with a circulating fan. Barley plants with heavily sporulating *Erysiphe graminis* lesions are placed in front of the fan to dislodge and distribute the spores. After two minutes the fan is shut off and the chamber is left closed five minutes for the spores to settle. Inoculated plants are then placed on an automatic sub-irrigation greenhouse bench.

Results are recorded seven days following inoculation as percent disease control based on the percent reduction in infected area as compared to the untreated control plants. Compound concentrations which provide 90% disease control (EC 90) are determined from dosage/dilution curves.

Leaf Rust (LR)

Seven seeds of Anza wheat are planted in 2" pots in a sandy-loam soil 12 days prior to testing. The compound to be tested is diluted with a 50/50 acetone/water solution to produce concentrations decreasing from 2250 µg/ml. Twelve ml of test solution are sprayed onto the wheat plants with an atomizing sprayer.

A suspension of *Puccinia recondita* urediospores is prepared by vacuuming spores from wheat leaves with ureida pustules and suspending 10⁵ spores/ml in deionized water plus 0.5% Tween ® 20 (polyoxyethylene sorbitan monolaurate). Plants are inoculated 24 hours after treatment by spraying with the spore suspension to runoff, allowing it to dry on the leaves, respraying to runoff, and then placing the plants into a mist chamber. Following 48 hours in the mist, plants are moved to a subirrigation greenhouse bench.

Results are recorded ten days following inoculation as percent disease control based on the percent reduction in lesion area as compared to the untreated control plants. Compound concentrations which provide 90% disease control (EC 90) are determined from dosage/dilution curves.

Botrytis Blight (BB)

Two white rose petals are placed in a petri dish lined with wet filter paper. The compound to be tested is diluted with a 50/50 acetone/water solution to produce concentrations decreasing from 2250 µg/ml. One-half ml of test solution is atomized onto the petals, and allowed to dry.

Inoculum is prepared by adding a 5 mm plug from a two-week old *Botrytis cinerea* culture grown on Elliot's V-8 agar, to 10 ml sterile distilled water plus 0.5 ml grape juice. A 20 µl drop of this inoculum suspension is placed on each petal. Petri dishes with inoculated petals are stored in sealed plastic boxes to maintain saturated humidity.

Results are read four days following inoculation as a percent reduction in necrotic area compared to the acetone/water controls. Compound concentrations which provide 90% disease control (EC 90) are determined from dosage/dilution curves.

Rice Blast (RB)

Ten seeds of Calrose M-9 rice are planted in a 2" pot in a sandy-loam soil 12 days prior to testing. The compound to be tested is diluted in a 50/50 acetone/water solution to produce concentrations decreasing from 2250 µg/ml and sprayed onto the rice plants with atomizing sprayers.

Inoculum is produced from 3 week old cultures of *Pyricularia oryzae*, grown on Rice Polish agar. The agar is first flooded with deionized water, the spores rubbed off the surface, and then diluted to 5×10⁵ spore/ml in deionized water+0.05% Tween 20. Plants are inoculated 24 hours after compound application by spraying with the spore suspension to runoff, allowing it to dry on the leaves, respraying to runoff, and then placing the plants into a dark mist chamber. Following 48 hours of mist, the plants are moved to an automatic subirrigation greenhouse bench.

Results are recorded seven days following inoculation as percent disease control based on the percent reduction in lesion area as compared to the untreated control plants. Compound concentrations which provide 90% disease control (EC 90) are estimated from dosage/dilution curves.

Late blight (LB)

Eight seeds of Ferry Morse Early-pak 707 tomatos are planted in a 2" pot in a sandy loam soil 15 days prior to testing. The compound to be tested is diluted with a 50/50 acetone/water solution to produce concentrations decreasing from 2250 μg/ml and sprayed onto the tomato plants with atomizing sprayers. Twenty-four hours later the plants are sprayed with a $10^5$ spore suspension of *Phytophthora infestans* sporangia and immediately placed in a mist chamber. After 48 hours in the mist, the plants are moved to a subirrigation greenhouse bench.

Results are recorded seven days following inoculation as percent disease control based on the percent reduction in lesion area as compared to the untreated control plants. Compound concentrations which provide 90% disease control (EC 90) are estimated from dosage/dilution curves.

The results are presented in Table II as an approximate EC 90 in parts per million. 2250 ppm equals 2250 μg/ml. The entry (750) indicates partial control at 750 ppm. A dash (-) indicates not tested. An asterisk (*) indicates no activity at 750 ppm. Most compounds were tested at a maximum of 750 ppm. Only selected compounds were tested at 2250 ppm. The entry (2250) indicates partial control at 2250 ppm.

TABLE II

| Cmpd. No. | PM | LR | BB | RB | LB |
|---|---|---|---|---|---|
| 1 | (750) | * | * | * | (750) |
| 2 | (750) | * | 500 | * | * |
| 3 | * | * | 250 | * | * |
| 4 | * | 750 | (750) | * | * |
| 5 | * | (750) | * | * | * |
| 6 | * | (750) | (750) | * | 750 |
| 7 | * | (750) | (750) | * | * |
| 8 | * | * | 25 | * | 750 |
| 9 | * | * | 80 | (750) | * |
| 10 | * | * | (750) | * | * |
| 11 | — | — | (750) | — | — |
| 12 | — | — | (750) | — | — |
| 13 | * | * | (750) | * | * |
| 14 | * | * | * | * | (750) |
| 15 | * | * | (750) | (750) | * |
| 16 | * | * | (750) | * | * |
| 17 | * | (750) | * | * | * |
| 18 | 750 | 750 | * | * | * |
| 19 | — | — | 750 | — | — |
| 20 | * | * | (750) | * | * |
| 21 | (750) | * | (750) | * | * |
| 22 | (2250) | 2250 | * | * | — |
| 23 | (2250) | 2250 | ** | * | — |
| 24 | * | * | (750) | * | — |
| 25 | (2250) | 2250 | (2250) | * | — |
| 26 | (750) | 750 | 400 | * | — |
| 27 | (750) | (750) | 250 | * | — |

The compounds of this invention are particularly effective against Botrytis Blight and are particularly effective as preventative foliar sprays and curative foliar sprays when compared to standard commercial compounds used as Botrytis preventative and curative sprays. Fungi on which the compounds of the present invention are particularly effective are as follows: *Botrytis cinerea; Septoria nodorum; Erysiphe graminis; Piricularia oryzae;* and *Puccinia graminis.*

The compounds of the present invention are useful as fungicides, especially as preventative or curative fungicides, and can be applied in a variety of ways at various concentrations. In general, these compounds and formulations of these compounds can be applied directly to the crop foliage, the soil in which the crop is growing, or in the irrigation water for the crop or soil. In practice, the compounds herein defined are formulated into fungicidal compositions, by admixture, in fungicidally effective amounts, with the adjuvants and carriers normally employed for facilitating the dispersion of active ingredients for agricultural applications, recognizing the fact that the formulation and mode of application of a toxicant may affect the activity of the materials in a given application. Thus, these active fungicidal compounds may be formulated as wettable powders, as emulsifiable concentrates, as powdery dusts, as solutions or as any of several other known types of formulations, depending upon the desired mode of application. Preferred formulations for preventative or curative fungicidal applications are wettable powders and emulsifiable concentrates. These formulations may contain as little as about 0.1% to as much as about 95% or more by weight of active ingredient. A fungicidally effective amount depends upon the nature of the seeds or plants to be treated and the rate of application varies from about 0.05 to approximately 25 pounds per acre, preferably from about 0.1 to about 10 pounds per acre.

Wettable powders are in the form of finely divided particles which disperse readily in water or other dispersants. The wettable powder is ultimately applied to the soil or plant either as a dry dust or as a dispersion in water or other liquid. Typical carriers for wettable powders include fuller's earth, kaolin clays, silicas and other readily wet organic or inorganic diluents. Wettable powders normally are prepared to contain about 5% to about 95% of the active ingredient and usually also contain a small amount of wetting, dispersing, or emulsifying agent to facilitate wetting and dispersion.

Dry flowables or water dispersible granules are agglomerated wettable powders made by either pan granulation or by fluidized bed. The dry flowable is ultimately applied to the soil or plant as a dispersion in water or other liquid. These granules are dust-free and free flowing when dry and yet upon dilution in water, form homogeneous dispersions. Typical carriers for dry flowables include fuller's earth, kaolin clays, silicas and other readily wet organic or inorganic diluents. The dry flowables normally are prepared to contain from about 5% to about 95% of the active ingredient and usually contain a small amount of wetting, dispersing or emulsifying agent to facilitate wetting and dispersion.

Emulsifiable concentrates are homogeneous liquid compositions which are dispersible in water or other dispersant, and may consist entirely of the active compound with a liquid or solid emulsifying agent, or may also contain a liquid carrier, such as xylene, heavy aromatic naphtha, isophorone and other non-volatile organic solvents. For fungicidal application, these concentrates are dispersed in water or other liquid carrier and normally applied as a spray to the area to be treated. The percentage by weight of the essential active ingredient may vary according to the manner in which the composition is to be applied, but in general comprises about 0.1% to 95% of active ingredient by weight of the fungicidal composition.

Typical wetting, dispersing or emulsifying agents used in agricultural formulations include, for example, the alkyl and alkylaryl sulfonates and sulfates and their sodium salts; polyhydroxy alcohols; and other types of surface-active agents, many of which are available in commerce. The surface-active agent, when used, normally comprises from 0.1% to 15% by weight of the fungicidal composition.

Dusts, which are free-flowing admixtures of the active ingredient with finely divided solids such as talc, clays, flours and other organic and inorganic solids which act as dispersants and carriers for the toxicant, are useful formulations for many applications.

Pastes, which are homogeneous suspensions of a finely divided solid toxicant in a liquid carrier such as water or oil, are employed for specific purposes. These formulations normally contain about 5% to about 95% of active ingredient by weight, and may also contain small amounts of a wetting, dispersing or emulsifying agent to facilitate dispersion. For application, the pastes are normally diluted and applied as a spray to the area to be affected.

EXAMPLES OF TYPICAL FORMULATIONS

| Ingredient | Weight % | | |
|---|---|---|---|
| Oil | | | |
| Compound 1 | 1 | | |
| Oil solvent-heavy aromatic naphtha | 99 | | |
| Total | 100 | | |
| Emulsifiable Concentrate | | | |
| Compound 2 | 50 | | |
| Kerosene | 45 | | |
| Emulsifying agent (mixture of long chain ethoxylated polyethers with long chain sulfonate) | 5 | | |
| Total | 100 | | |
| Emulsifiable Concentrate | | | |
| Compound 3 | 90 | | |
| Kerosene | 5 | | |
| Emulsifying agent (mixture of long chain ethoxylated polyethers with long chain sulfonate) | 5 | | |
| Total | 100 | | |
| Dusts and/or Powders | | | |
| Ingredient | Wt. % | Wt. % | Wt. % |
| Compound 4 | 0.5 | 50.0 | 90.0 |
| Attapulgite Clay Powder | 93.5 | 44.0 | 4.0 |
| Sodium lignin sulfonate | 5.0 | 5.0 | 5.0 |
| Sodium dioctyl sulfosuccinate | 1.0 | 1.0 | 1.0 |
| Total | 100.0 | 100.0 | 100.0 |

Other useful formulations for fungicidal applications include simple solutions of the active ingredient in a dispersant in which it is completely soluble at the desired concentration, such as acetone, alkylated naphthalenes, xylene and other organic solvents. Pressurized sprays, typically aerosols, wherein the active ingredient is dispersed in finely divided form as a result of vaporization of a low boiling dispersant solvent carrier, such as the Freons, may also be used.

The fungicidal compositions of this invention are applied to the plants in the conventional manner. Thus, the dust and liquid compositions can be applied to the plant by the use of power-dusters, boom and hand sprayers and spray dusters. The compositions can also be applied from airplanes as a dust or a spray because they are effective in low dosages.

We claim:
1. A compound having the structural formula

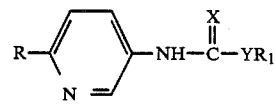

wherein
R is selected from the group consisting of halogen, $C_1$-$C_3$ alkoxy, —$CF_3$, $C_3$-$C_4$ alkenyloxy and $C_1$-$C_3$ haloalkoxy;
$R_1$ is selected from the group consisting of $C_1$-$C_6$ alkyl, $C_3$-$C_6$ cycloalkyl, benzyl, $C_1$-$C_3$ haloalkyl, and $C_3$-$C_8$ cyclic, straight or branched alkoxyalkyl;
X is either oxygen or sulfur; Y is either oxygen or sulfur; or a fungicidally acceptable organic or inorganic salt thereof.

2. The compound of claim 1 wherein R is —$OCH_2CH=CH_2$, $R_1$ is —$C_2H_5$, X is O and Y is S.

3. The compound of claim 1 wherein R is —$OCH_3$, $R_1$ is —$CH_3$, X is O and Y is O.

4. The compound of claim 1 wherein R is $OCH_3$, $R_1$ is —$C_2H_5$, X is O and Y is O.

5. A fungicidal composition comprising a fungicidally effective amount of a compound having the structural formula

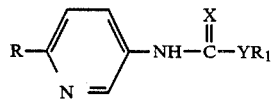

wherein
R is selected from the group consisting of halogen, $C_1$-$C_3$ alkoxy, —$CF_3$, $C_3$-$C_4$ alkenyloxy and $C_1$-$C_3$ haloalkoxy;
$R_1$ is selected from the group consisting of $C_1$-$C_6$ alkyl, $C_3$-$C_6$ cycloalkyl, benzyl, $C_1$-$C_3$ haloalkyl, and $C_3$-$C_8$ cyclic, straight or branched alkoxyalkyl;
X is either oxygen or sulfur; Y is either oxygen or sulfur; or a fungicidally acceptable organic or inorganic salt thereof and an inert diluent carrier.

6. The method of controlling fungi comprising applying to the area where control is desired, a fungicidally effective amount of a compound having the formula

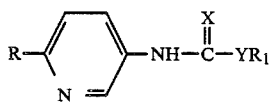

wherein
R is selected from the group consisting of halogen, $C_1$-$C_3$ alkoxy, —$CF_3$, $C_3$-$C_4$ alkenyloxy and $C_1$-$C_3$ haloalkoxy;
$R_1$ is selected from the group consisting of $C_1$-$C_6$ alkyl, $C_3$-$C_6$ cycloalkyl, benzyl, $C_1$-$C_3$ haloalkyl, and $C_3$-$C_8$ cyclic, straight or branched alkoxyalkyl;
X is either oxygen or sulfur; Y is either oxygen or sulfur; or a fungicidally acceptable organic or inorganic salt thereof.

7. The method of claim 6 wherein R is —$OCH_2CH=CH_2$, $R_1$ is —$C_2H_5$, X is O and Y is S.

8. The method of claim 6 wherein R is —$OCH_3$, $R_1$ is —$CH_3$, X is O and Y is O.

9. The method of claim 6 wherein R is $OCH_3$, $R_1$ is —$C_2H_5$, X is O and Y is O.

* * * * *